(12) United States Patent
Aihara et al.

(10) Patent No.: US 7,863,460 B2
(45) Date of Patent: Jan. 4, 2011

(54) PROCESS FOR PRODUCING 1-SUBSTITUTED-3-FLUOROALKYLPYRAZOLE-4-CARBOXYLATE

(75) Inventors: Hidenori Aihara, Kanagawa (JP); Wakako Yokota, Kanagawa (JP); Tetsu Yamakawa, Tokyo (JP); Kenji Hirai, Kanagawa (JP)

(73) Assignees: Sagami Chemical Research Center, Kanagawa (JP); Japan Finechem Company, Inc., Tokyo (JP)

( * ) Notice: Subject to any disclaimer, the term of this patent is extended or adjusted under 35 U.S.C. 154(b) by 594 days.

(21) Appl. No.: 11/884,665

(22) PCT Filed: Feb. 23, 2006

(86) PCT No.: PCT/JP2006/303269

§ 371 (c)(1), (2), (4) Date: Oct. 1, 2007

(87) PCT Pub. No.: WO2006/090778

PCT Pub. Date: Aug. 31, 2006

(65) Prior Publication Data

US 2008/0154045 A1 Jun. 26, 2008

(30) Foreign Application Priority Data

Feb. 25, 2005 (JP) .............................. 2005-052004
Feb. 25, 2005 (JP) .............................. 2005-052006

(51) Int. Cl.
*C07D 231/14* (2006.01)
(52) U.S. Cl. .................................................. 548/374.1
(58) Field of Classification Search ............... 548/374.1
See application file for complete search history.

(56) References Cited

FOREIGN PATENT DOCUMENTS

| JP | 8-269014 A | 10/1996 |
|---|---|---|
| JP | 10-175957 A | 6/1998 |
| JP | 2001-58982 A | 3/2001 |
| WO | WO 2004/060877 A1 | 7/2004 |
| WO | WO 2004073594 A2 * | 9/2004 |
| WO | WO 2005003077 A1 * | 1/2005 |
| WO | WO 2005/123690 A1 | 12/2005 |

\* cited by examiner

*Primary Examiner*—Yong Chu
(74) *Attorney, Agent, or Firm*—Sughrue Mion, PLLC

(57) ABSTRACT

In a process for producing 1-substituted-3-fluoroalkyl-pyrazole-4-carboxylate (3) by a reaction of 2-alkoxymethylene-fluoroacylacetate (1) and hydrazine (2), the reaction is conducted in the presence of a base and water, to produce 1-substituted-3-fluoroalkylpyrazole-4-carboxylate (3) with high selectivity and yield. This novel process enables to produce 1-substituted-3-fluoroalkylpyrazole-4-carboxylate (3), which is useful as an intermediate for pharmaceuticals and agrochemicals, with high selectivity and yield by simple and safe operations.

6 Claims, No Drawings

PROCESS FOR PRODUCING 1-SUBSTITUTED-3-FLUOROALKYLPYRAZOLE-4-CARBOXYLATE

TECHNICAL FIELD

The present invention relates to a process for producing 1-substituted-3-fluoroalkylpyrazole-4-carboxylate represented by the following general formula (3), which is useful as a synthetic intermediate for pharmaceuticals and agrochemicals.

[Formula 1]

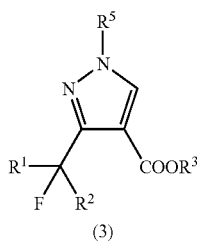

(3)

wherein $R^1$ represents a hydrogen atom or a halogen atom, $R^2$ represents a hydrogen atom, a fluorine atom or an alkyl group having 1 to 12 carbon atoms, which may be substituted with a chlorine atom or a fluorine atom, $R^3$ represents an alkyl group having 1 to 6 carbon atoms, and $R^5$ represents an alkyl group having 1 to 6 carbon atoms.

BACKGROUND ART

It is known that generally, in a reaction of 2-alkoxymethyleneacylacetate and substituted hydrazine, there are plurality of reaction sites in 2-alkoxymethyleneacylacetate as each reaction substrate, which causes inferior selectivity of the reaction to form 1,3-disubstituted-pyrazole-4-carboxylate and 1,5-disubstituted-pyrazole-4-carboxylate which is regioisomer thereof as a by-product. Accordingly, in order to obtain the desired pyrazole derivative, a purification process such as silica gel column chromatography, which is difficult to be industrially performed, is usually required. In JP-A-2000-128763 (patent document 1), it is described that a mixture of 1,3- and 1,5-disubstituted-pyrazole-4-carboxylates obtained as a mixture are hydrolyzed, followed by crystallization to give the desired 1,3-disubstituted-pyrazole-4-carboxylic acid. However, in order to obtain the desired product of high purity, it is necessary to perform crystallization under strict pH control, which industrially causes necessity of complicated operations.

In JP-A-1-113371 (patent document 2), there is described a production method of 1,3-disubstituted-pyrazole-4-carboxylate by a reaction of 2-ethoxymethyleneacylacetate and substituted hydrazine. However, there is no detailed description for the yield and selectivity of 1-substituted-3-trifluoromethylpyrazole-4-carboxylate in the present invention.

The present inventors have conducted a reaction of ethyl 2-ethoxymethylene-4,4,4-trifluoroacetoacetate and methylhydrazine by using the method described in patent document 2. As a result, the isomer ratio of ethyl 1-methyl-3-trifluoromethylpyrazole-4-carboxylate and its regioisomer of ethyl 1-methyl-5-trifluoromethylpyrazole-4-carboxylate is 76:24, and it is therefore difficult to say that the procedure is a method having good selectivity (see the following Comparative Example 3).

Further, in Example 1 of JP-A-6-199803 (patent document 3), there is described a method of producing ethyl 1-methyl-3-trifluoromethylpyrazole-4-carboxylate by reacting ethyl-2-ethoxymethylene-4,4,4-trifluoroacetoacetate with methylhydrazine in ethanol at a specified temperature. However, it is clearly written that the desired product is obtained as a mixture containing 15% of undesired ethyl-1-methyl-5-trifluoromethylpyrazole-4-carboxylate. Furthermore, according to the method described in this patent, raw materials are required to be charged at a low temperature of −40 to −35° C., so that this method is industrially lacking in economic efficiency.

Further, in JP-A-2000-212166 (patent document 4), there is described a production method of 1-substituted-3-trifluoromethylpyrazole-4-carboxylate using 2-ethoxy-methylene-4,4,4-trifluoroacetoacetate and substituted hydrazine. It is described that 1-substituted-3-trifluoromethylpyrazole-4-carboxylate is obtained in a yield of about 85% according to this method (Examples 2 to 4). On the other hand, there is no description for the formation of 1-substituted-5-trifluoromethylpyrazole-4-carboxylate, which is an isomer. However, it is clearly written in the specification that when 2-ethoxymethyleneacylacetate and alkylhydrazine are allowed to react with each other at 10° C., a mixture of the desired 1,3-dialkylpyrazole-4-carboxylate (yield: 80~85%) and its regioisomer 1,5-dialkylpyrazole-4-carboxylate (yield: 10~15%) is obtained, which causes the necessity of purification by distillation in order to obtain the desired product. Furthermore, in the method of this patent, usable solvents are limited, and it is indispensable to conduct the reaction in esters as a solvent (for example, ethyl acetate or dimethyl carbonate). In addition, in order to obtain the desired product with high yield, it is necessary to conduct the reaction at a low temperature of 5 to 10° C. in the beginning of the reaction, and thereafter, at a reflux temperature of the solvent used. Accordingly, it is hard to say to be an industrially advantageous production method.

Moreover, in the methods described in JP-A-1-113371 (patent document 2), JP-A-6-199803 (patent document 3) and JP-A-2000-212166 (patent document 4) mentioned above, anhydrous hydrazines are used as the raw materials. However, anhydrous hydrazines are highly explosive as is well known, so that it is highly dangerous to use them in large amounts on an industrial scale. Accordingly, when the desired 1,3-disubstituted-pyrazole-4-carboxylate can be highly selectively produced with high yield by using hydrazine hydrate or aqueous solution of hydrazine having low explosive properties, it can conceivably become an extremely excellent method as an industrial production method. However, in all of the above-mentioned patent documents 2 to 4, the influence of water on the yield and selectivity of the desired 1,3-disubstituted-pyrazole-4-carboxylate at the time when water coexists in the reaction system is not described at all. Further, as a result that this reaction has been actually conducted in the presence of water, it has become clear that selectivity substantially decreases. It has therefore been revealed that the desired 1,3-disubstituted-pyrazole-4-carboxylate is not necessarily obtained in good selectivity only by conducting the reaction in the presence of water (see the following Comparative Examples 1, 5, 6 and 7).

Patent Document 1: JP-A-2000-128763
Patent Document 2: JP-A-1-113371
Patent Document 3: JP-A-6-199803 (DE4231517A1)
Patent Document 4: JP-A-2000-212166

DISCLOSURE OF THE INVENTION

Problems that the Invention is to Solve

The present invention provides a new process for producing 3-fluoroalkylpyrazole-4-carboxylate (3) as a useful intermediate for pharmaceuticals and agrochemicals, which is one of the two kinds of regioisomers, 3-fluoroalkylpyrazole-4-carboxylate (3) and 5-fluoroalkylpyrazole-4-carboxylate (4), by a reaction of 2-alkoxymethylenefluoroacylacetate (1) and hydrazine (2) with high yield and selectivity by simple and safe operations according to the following reaction scheme.

[Formula 2]

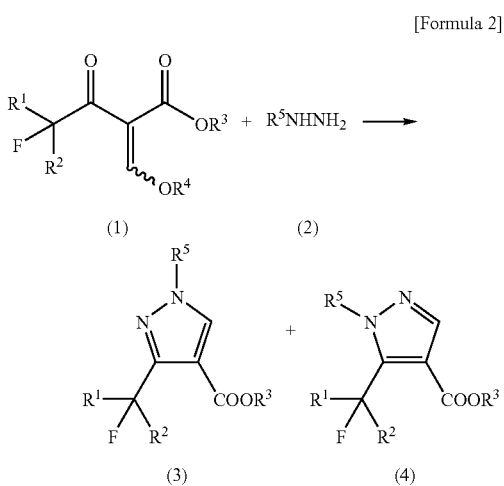

wherein $R^1$ represents a hydrogen atom or a halogen atom, $R^2$ represents a hydrogen atom, a fluorine atom or an alkyl group having 1 to 12 carbon atoms, which may be substituted with a chlorine atom or a fluorine atom, $R^3$ and $R^4$ each independently represents an alkyl group having 1 to 6 carbon atoms, and $R^5$ represents an alkyl group having 1 to 6 carbon atoms, which may be substituted.

Means for Solving the Problems

The present inventors have made intensive studies to solve the above-mentioned problems. As a result, in the above-mentioned reaction, it has been found that the desired 1-substituted-3-fluoroalkylpyrazole-4-carboxylate can be selectively produced with high yield by conducting the reaction in the presence of a base and in a water solvent or a mixed solvent of water and an organic solvent, thus completing the present invention.

That is to say, the present invention relates to a new process for production which is characterized in that 2-alkoxymethylenefluoroacylacetate represented by general formula (1):

[Formula 3]

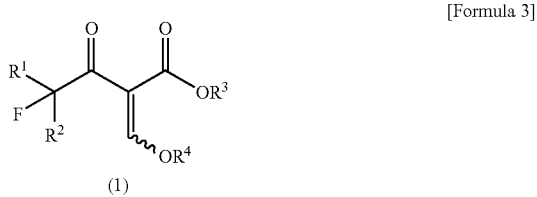

wherein $R^1$, $R^2$, $R^3$ and $R^4$ have the same meanings as described above, and hydrazine represented by general formula (2):

[Formula 4]

$$R^5NHNH_2 \qquad (2)$$

wherein $R^5$ has the same meaning as described above, are reacted with each other in the presence of a base and in a water solvent or a mixed solvent of water and an organic solvent, thereby producing 1-substituted-3-fluoroalkylpyrazole-4-carboxylate represented by general formula (3):

[Formula 5]

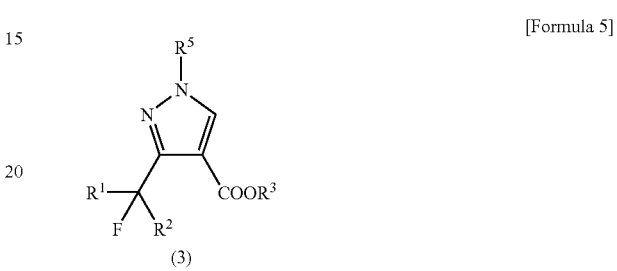

wherein $R^1$, $R^2$, $R^3$ and $R^5$ have the same meanings as described above.

The above-mentioned base as used herein is preferably sodium hydroxide or potassium hydroxide.

Further, the amount of the above-mentioned base used is preferably from 0.001 to 10.0 equivalents based on 2-alkoxymethylenefluoroacylacetate (1) as a reaction substrate.

Furthermore, the weight ratio of 2-alkoxy-methylenefluoroacylacetate (1) represented by general formula (1) and water is preferably from 1/0.25 to 1/100. Moreover, the above-mentioned organic solvent is preferably at least one selected from the group of aromatic hydrocarbons, aliphatic hydrocarbons, alcohols, esters and halogenated hydrocarbons.

In addition, the reaction temperature is preferably from −30 to 80° C.

ADVANTAGES OF THE INVENTION

According to the process for producing 1-substituted-3-fluoroalkylpyrazole-4-carboxylate of the present invention, conventional problems are overcome, and the desired product can be highly selectively produced with high yield by simple and safe operations. 3-Fluoroalkylpyrazole-4-carboxylate, which can be produced by the process of the present invention is particularly useful as an intermediate for pharmaceuticals and agrochemicals, and the present invention provides the industrially extremely useful process.

BEST MODE FOR CARRYING OUT THE INVENTION

The process of the present invention will be described in more detail below.

Some of 2-alkoxymethylenefluoroacylacetate (1) used as a raw material in the process of the present invention is commercially available, but it can be easily produced by usual synthetic methods in organic chemistry. For example, it can be easily produced by reaction of β-ketocarboxylate, which is obtained by Claisen condensation of fluorine-containing carboxylate and acetate, with orthoformate in the presence of acetic anhydride.

Here, examples of the substituents represented by $R^1$, $R^2$, $R^3$, $R^4$ and $R^5$ in the above-mentioned general formulas (1) to (3) will be shown below.

A halogen atom represented by $R^1$ is exemplified by a fluorine atom, a chlorine atom, a bromine atom or the like.

An alkyl group having 1 to 12 carbon atoms represented by $R^2$, which may be substituted with a chlorine atom or a fluorine atom, is exemplified by a trifluoromethyl group, a di-fluoromethyl group, a chlorodifluoromethyl group, a penta-fluoroethyl group, a perfluoropropyl group, a perfluoropentyl group, a 1,1,2,2,3,3,4,4,5,5-decafluoropentyl group, a perfluorohexyl group, a perfluorononyl group, a perfluorodecyl group or a perfluorododecyl group or the like.

An alkyl groups having 1 to 6 alkyl groups represented by $R^3$ and $R^4$ of general formula (1) include a methyl group, an ethyl group, a propyl group, an isopropyl group, a butyl group, isobutyl group, a pentyl group or a hexyl group and the like.

Further, as an alkyl group having 1 to 6 carbon atoms represented by $R^5$ shown in general formula (2), which may be substituted, there can be exemplified a methyl group, an ethyl group, a propyl group, a cyclopropylmethyl group, a butyl group, an isobutyl group, a pentyl group or a hexyl group or the like. Furthermore, these alkyl groups may be substituted with one or more halogen atoms or the like, and specifically, examples thereof include a 2-chloroethyl group, a 2-bromoethyl group, a 2-hydroxyethyl group, a 2,2,2-trifluoroethyl group or a 3-chloropropyl group and the like.

Hydrazines used as a raw material in the present process are partially easily available, and can be easily produced by conventional methods. Further, these hydrazines can be used in any form of an anhydride, a hydrate and an aqueous solution.

In the process of the present invention, it is indispensable to conduct the reaction in the presence of a base and water.

As the base, there can be used alkali metal hydroxides such as lithium hydroxide, sodium hydroxide or potassium hydroxide, alkali earth metal hydroxides such as calcium hydroxide, or organic amines such as triethylamine, N-methylmorpholine or pyridine. Sodium hydroxide or potassium hydroxide is preferred among others in terms of the good yield and selectivity of the desired product and its cheapness.

There is no particular limitation of the base on the amount thereof used and the concentration of an aqueous solution thereof. It is used in an amount of 0.001 to 10.0 equivalents, and preferably in an amount of 0.05 to 5.0 equivalents, based on the above-mentioned 2-alkoxymethylenefluoroacylacetate (1), thereby being able to obtain the desired product with the good yield and selectivity.

Further, although there is no particular limitation on the amount of water used, it is preferred to conduct the reaction, under control of the amount of water added, because a hydrolysis reaction occurs in ester units of the raw material or the product, depending on the reaction conditions, when the reaction is conducted in an aqueous solution of inorganic base. As for the amount of water used, the weight ratio of 2-alkoxy-methylenefluoroacylacetate (1) and water is preferably from 1/0.25 to 1/100, and desirably from 1/1 to 1/50, in terms of the good yield and selectivity.

Further, in the process of the present invention, the reaction can also be conducted under the coexistence of an organic solvent. As the organic solvent, there can be exemplified aromatic hydrocarbons such as benzene, toluene, xylene, chlorobenzene or dichlorobenzene, aliphatic hydrocarbons such as pentane, hexane or octane, halogenated hydrocarbons such as dichloromethane, chloroform, carbon tetrachloride or 1,2-dichloroethane, esters such as ethyl acetate, butyl acetate or dimethyl carbonate, alcohols such as methanol, ethanol, propyl alcohol, isopropyl alcohol, butyl alcohol or tert-butyl alcohol, ethers such as diethyl ether, diisopropyl ether, cyclopentyl methyl ether, 1,2-di-methoxyethane, tetrahydrofuran or 1,4-dioxane, or the like. Preferred are aromatic hydrocarbons, aliphatic hydrocarbons, alcohols and halogenated hydrocarbons. There is no particular limitation on the amount of the organic solvent used.

Further, the reaction is conducted at a reaction temperature appropriately selected from −30 to 80° C., preferably from −20 to 60° C., thereby being able to obtain the desired product with the good yield and selectivity. However, in the reaction in water solvent, it is preferred to conduct the reaction at a temperature at which water is not solidified or higher.

EXAMPLES

The present invention will be illustrated in greater detail with reference to the following examples and comparative examples, but the invention should not be construed as being limited thereto.

Example 1

Ethyl 1-methyl-3-trifluoromethylpyrazole-4-carboxylate was produced according to the following reaction formula:

[Formula 6]

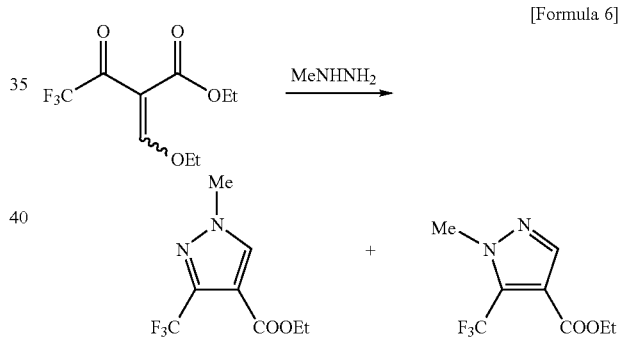

A 35% by weight aqueous solution of methylhydrazine (0.197 mL, 1.5 mmol) was added to a solution of potassium hydroxide (28 mg, 0.5 mmol) in water (5.0 mL) with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (90 mg, yield: 81%) composed of ethyl 1-methyl-3-trifluoromethylpyrazole-4-carboxylate and ethyl 1-methyl-5-trifluoromethyl-pyrazole-4-carboxylate. Gas chromatography (GC) analysis revealed that the ratio of the former and the latter was 93:7.

Ethyl 1-methyl-3-trifluoromethylpyrazole-4-carboxylate; $^1$H-NMR (CDCl$_3$, TMS, ppm): δ1.32 (t, J=10 Hz, 3H), 3.97 (s, 1H), 4.32 (q, J=6.7 Hz, 2H), 7.96 (s, 1H)

Ethyl 1-methyl-5-trifluoromethylpyrazole-4-carboxylate; $^1$H-NMR (CDCl$_3$, TMS, ppm): δ1.35 (t, J=7.1 Hz, 3H), 4.07 (s, 3H), 4.32 (q, J=7.2 Hz, 2H), 7.90 (s, 1H)

Example 2

A 35% by weight aqueous solution of methylhydrazine (0.197 mL, 2.3 mmol) was added to a solution of sodium hydroxide (20 mg, 0.5 mmol) in water (5.0 mL) with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (96 mg, yield: 86%) composed of ethyl 1-methyl-3-trifluoro-methylpyrazole-4-carboxylate and ethyl 1-methyl-5-trifluoro-methylpyrazole-4-carboxylate. GC analysis revealed that the ratio of the former and the latter was 98:2.

Example 3

Methylhydrazine (10.6 mL, 200 mmol) was added to a solution of potassium hydroxide (4.4 g, 78.4 mmol) in water (100 mL) with stirring. To the solution, ethyl 2-ethoxy-methylene-4,4,4-trifluoroacetoacetate (16.0 g, 66.7 mmol) was added dropwise under ice-cooling, taking about 30 minutes, followed by stirring for 1 hour at ambient temperature. After the reaction was completed, a solid deposited was taken by filtration, fully washed with water, and then, dried, thereby obtaining a white solid (10.4 g, yield: 70%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 99:1.

Example 4

A 35% by weight aqueous solution of methylhydrazine (1.6 mL, 18.7 mmol) was added to a solution of sodium hydroxide (177 mg, 4.42 mmol) in water (41.5 mL) with stirring. To the solution, ethyl 2-ethoxymethylenetrifluoroacetoacetate (1.0 g, 4.16 mmol) was added dropwise under ice-cooling, taking about 25 minutes, followed by stirring at the same temperature for 10 minutes. To the reaction mixture, 1N hydrochloric acid (20 mL) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture composed of ethyl 1-methyl-3-trifluoro-methylpyrazole-4-carboxylate and ethyl 1-methyl-5-trifluoro-methylpyrazole-4-carboxylate approximately quantitatively. GC analysis revealed that the ratio of the former and the latter was 91:9.

Example 5

A 35% by weight aqueous solution of methylhydrazine (1.6 mL, 18.7 mmol) was added to a solution of sodium hydroxide (176 mg, 4.40 mmol) in water (20 mL) with stirring. To the solution, ethyl 2-ethoxymethylenetrifluoroacetoacetate (1.0 g, 4.16 mmol) was added dropwise under ice-cooling, taking about 25 minutes, followed by stirring at the same temperature for 1 hour. To the reaction mixture, 1N hydrochloric acid (20 ml) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (872 mg, yield: 94%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 90:10.

Example 6

Water (41.5 mL) and a 35% by weight aqueous solution of methylhydrazine (0.5 mL, 5.84 mmol) were added to an 18% aqueous solution of sodium hydroxide (0.8 mL, 4.4 mmol) with stirring. To the solution, ethyl 2-ethoxymethylenetrifluoroacetoacetate (1.0 g, 4.16 mmol) was added dropwise under ice-cooling, taking about 20 minutes, followed by stirring at the same temperature for 10 minutes. To the reaction mixture, 1N hydrochloric acid (20 mL) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (788 mg, yield: 85%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 91:9.

Example 7

Methylhydrazine (0.57 mL, 10.8 mmol) was added to a solution of sodium hydroxide (167 mg, 4.17 mmol) in water (6 mL) with stirring. To the solution, ethyl 2-ethoxymethylenetrifluoroacetoacetate (1.0 g, 4.16 mmol) was added dropwise under ice-cooling, taking about 10 minutes, followed by stirring for 10 minutes at the same temperature. After the reaction was completed, a solid deposited was taken by filtration, fully washed with water, and then, dried, thereby obtaining a white solid (556 mg, yield: 60%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 98:2.

Example 8

Sodium hydroxide (20 mg, 0.5 mmol) was dissolved in a mixed solvent of toluene (2.5 mL) and water (2.5 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise under ice-cooling, taking about 5 minutes, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer obtained was dried over anhydrous sodium sulfate, and the desiccant was separated by filtration. Then, the filtrate was evaporated to dryness under reduced pressure, thereby obtaining a white solid (95 mg, yield: 86%) composed of ethyl 1-methyl-3-trifluoromethylpyrazole-4-carboxylate and ethyl 1-methyl-5-trifluoromethylpyrazole-4-carboxylate. $^1$H-NMR spectra revealed that the ratio of the former and the latter was 98:2.

Example 9

Water (10 mL) and a 35% by weight aqueous solution of methylhydrazine (0.5 mL, 5.84 mmol) were added to an 18% aqueous solution of sodium hydroxide (0.8 mL, 4.4 mmol) with stirring. To the solution, a toluene solution (10 mL) of ethyl 2-ethoxymethylenetrifluoroacetoacetate (1.0 g, 4.16 mmol) was added dropwise at −20° C., taking about 5 minutes, followed by stirring at the same temperature for 10 minutes. To the reaction mixture, 1N hydrochloric acid (20 ml) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (733 mg, yield: 79%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 91:9.

Example 10

The reaction was conducted in the same manner as in Example 9 with the exception that the reaction temperature was 10° C., thereby obtaining a mixture (820 mg, yield: 89%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 91:9.

Example 11

A 35% by weight aqueous solution of methylhydrazine (0.55 mL, 6.43 mmol) was added to a solution of sodium hydroxide (169 mg, 4.22 mmol) in water (2.0 mL) with stirring. To the solution, a toluene solution (10 mL) of ethyl 2-ethoxymethylenetri-fluoroacetoacetate (1.0 g, 4.16 mmol) was added dropwise at 25° C., taking about 5 minutes, followed by stirring at the same temperature for 10 minutes. The reaction mixture was extracted with toluene (20 mL×3), and the organic layer was dried over anhydrous magnesium sulfate. After the desiccant was separated by filtration, the solvent was removed from the filtrate by distillation under reduced pressure, thereby obtaining a mixture (829 mg, yield: 90%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 99:1.

Example 12

Methylhydrazine (0.2 mL, 3.80 mmol) was added to a solution of sodium hydroxide (168 mg, 4.20 mmol) in water (2.0 mL) with stirring. To the solution, a toluene solution (10 mL) of ethyl 2-ethoxymethylenetrifluoroacetoacetate (1.0 g, 4.16 mmol) was added dropwise at 50° C., taking about 5 minutes, followed by stirring at the same temperature for 10 minutes. The reaction mixture was extracted with toluene (20 mL×3), and the organic layer was dried over anhydrous magnesium sulfate. After the desiccant was separated by filtration, the solvent was removed from the filtrate by distillation under reduced pressure, thereby obtaining a mixture composed of ethyl 1-methyl-3-trifluoromethylpyrazole-4-carboxylate and ethyl 1-methyl-5-trifluoromethylpyrazole-4-carboxylate approximately quantitatively. GC analysis revealed that the ratio of the former and the latter was 96:4.

Example 13

Methylhydrazine (2.0 mL, 38.0 mmol) was added to a solution of sodium hydroxide (832 mg, 20.8 mmol) in water (20 mL) with stirring. To the solution, a toluene solution (100 mL) of ethyl 2-ethoxymethylenetrifluoroacetoacetate (10 g, 41.6 mmol) was added dropwise under ice-cooling, taking about 5 minutes, followed by stirring at the same temperature for 20 minutes. The reaction mixture was extracted with toluene (30 mL×4), and the organic layer was dried over anhydrous magnesium sulfate. After the desiccant was separated by filtration, the solvent was removed from the filtrate by distillation under reduced pressure, thereby obtaining a product (7.86 g, yield: 93%). GC analysis revealed that this was an approximately pure product of ethyl 1-methyl-3-trifluoromethylpyrazole-4-carboxylate.

Example 14

Methylhydrazine (2.0 mL, 38.0 mmol) was added to a solution of sodium hydroxide (1.7 g, 42.5 mmol) in water (10 mL) with stirring. To the solution, a toluene solution (100 mL) of ethyl 2-ethoxymethylenetrifluoroacetoacetate (10 g, 41.6 mmol) was added dropwise under ice-cooling, taking about 5 minutes, followed by stirring at the same temperature for 20 minutes. The reaction mixture was extracted with toluene (30 mL×4), and the organic layer was dried over anhydrous magnesium sulfate. After the desiccant was separated by filtration, the solvent was removed from the filtrate by distillation under reduced pressure, thereby obtaining a mixture (7.51 g, yield: 89%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 99:1.

Example 15

Methylhydrazine (0.20 mL, 3.80 mmol) was added to a solution of sodium hydroxide (610 mg, 15.2 mmol) in water (2.0 mL) with stirring. To the solution, a toluene solution (10 mL) of ethyl 2-ethoxymethylenetrifluoroacetoacetate (1.0 g, 4.16 mmol) was added dropwise under ice-cooling, taking about 5 minutes, followed by stirring at the same temperature for 10 minutes. The reaction mixture was extracted with toluene (20 mL×3), and the organic layer was dried over anhydrous magnesium sulfate. After the desiccant was separated by filtration, the solvent was removed from the filtrate by distillation under reduced pressure, thereby obtaining a mixture (749 mg, yield: 89%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 99:1.

Example 16

Methylhydrazine (0.21 mL, 3.99 mmol) was added to a solution of triethylamine (60 mg, 0.593 mmol) in water (2.0 mL) with stirring. To the solution, a toluene solution (10 mL)

of ethyl 2-ethoxymethylenetrifluoroacetoacetate (1.0 g, 4.16 mmol) was added dropwise under ice-cooling, taking about 5 minutes, followed by stirring at the same temperature for 10 minutes. The reaction mixture was extracted with toluene (20 mL×3), and the organic layer was dried over anhydrous magnesium sulfate. After the desiccant was separated by filtration, the solvent was removed from the filtrate by distillation under reduced pressure, thereby obtaining a mixture composed of ethyl 1-methyl-3-trifluoro-methylpyrazole-4-carboxylate and ethyl 1-methyl-5-tri-fluoromethylpyrazole-4-carboxylate approximately quantitatively. GC analysis revealed that the ratio of the former and the latter was 93:7.

Example 17

Methylhydrazine (231 mg, 5.01 mmol) was added to a solution of pyridine (36 mg, 0.455 mmol) in water (2.0 mL) with stirring. To the solution, a toluene solution (10 mL) of ethyl 2-ethoxymethylenetrifluoroacetoacetate (1.0 g, 4.16 mmol) was added dropwise under ice-cooling, taking about 5 minutes, followed by stirring at the same temperature for 10 minutes. To the reaction mixture, 2N hydrochloric acid (3 ml) was added, followed by extraction with toluene (20 mL×3). The organic layer was dried over anhydrous magnesium sulfate, and the desiccant was separated by filtration. The solvent was removed from the filtrate by distillation under reduced pressure, thereby obtaining a mixture (842 mg, yield: 91%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 90:10.

Example 18

Potassium hydroxide (28 mg, 0.5 mmol) was dissolved in a mixed solvent of ethanol (4.75 mL) and water (0.25 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer obtained was dried over anhydrous sodium sulfate. After the desiccant was separated by filtration, the filtrate was evaporated to dryness under reduced pressure, thereby obtaining a white solid (91 mg, yield: 82%) composed of ethyl 1-methyl-3-trifluoro-methylpyrazole-4-carboxylate and ethyl 1-methyl-5-trifluoro-methylpyrazole-4-carboxylate. $^1$H-NMR spectra revealed that the ratio of the former and the latter was 93:7.

Example 19

Potassium hydroxide (28 mg, 0.5 mmol) was dissolved in a mixed solvent of ethanol (4.75 mL) and water (0.25 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise at room temperature with stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer obtained was dried over anhydrous sodium sulfate, and the desiccant was separated by filtration. Then, the filtrate was evaporated to dryness under reduced pressure, thereby obtaining a white solid (87 mg, yield: 78%) composed of ethyl 1-methyl-3-trifluoromethylpyrazole-4-carboxylate and ethyl 1-methyl-5-trifluoromethylpyrazole-4-carboxylate. $^1$H-NMR spectra revealed that the ratio of the former and the latter was 91:9.

Example 20

Sodium hydroxide (20 mg, 0.5 mmol) was dissolved in a mixed solvent of hexane (2.5 mL) and water (2.5 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer obtained was dried over anhydrous sodium sulfate, and the desiccant was separated by filtration. Then, the filtrate was evaporated to dryness under reduced pressure, thereby obtaining a white solid (92 mg, yield: 83%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 98:2.

Example 21

Methylhydrazine (0.19 mL, 3.61 mmol) was added to a 20% aqueous solution of sodium hydroxide (0.8 mL, 4.40 mmol) in water (5.0 mL), and tetrabutylammonium bromide (14 mg, 0.043 mmol) was further added to the solution with stirring. To the solution, a toluene solution (5.0 mL) of ethyl 2-ethoxymethylenetrifluoroacetoacetate (1.0 g, 4.16 mmol) was added dropwise under ice-cooling, taking about 15 minutes, followed by stirring at the same temperature for 10 minutes. To the reaction mixture, 1N hydrochloric acid (20 mL) was added, followed by extraction with ethyl acetate (30 mL×3). The organic layer was dried over anhydrous magnesium sulfate, and the desiccant was separated by filtration. Then, the solvent was removed from the filtrate by distillation under reduced pressure, thereby obtaining a mixture composed of ethyl 1-methyl-3-trifluoromethylpyrazole-4-carboxylate and ethyl 1-methyl-5-trifluoromethylpyrazole-4-carboxylate approximately quantitatively. GC analysis revealed that the ratio of the former and the latter was 90:10.

Example 22

Sodium hydroxide (20 mg, 0.5 mmol) was dissolved in a mixed solvent of chloroform (2.5 mL) and water (2.5 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer obtained was dried over anhydrous sodium sulfate, and the desiccant was separated by filtration. Then, the filtrate was evaporated to dryness under reduced pressure, thereby obtaining a white solid (105 mg, yield: 95%) composed of ethyl 1-methyl-3-trifluoro-methylpyrazole-4-carboxylate and ethyl 1-methyl-5-trifluoro-methylpyrazole-4-carboxylate. GC analysis revealed that the ratio of the former and the latter was 98:2.

Example 23

Sodium hydroxide (20 mg, 0.5 mmol) was dissolved in a mixed solvent of chlorobenzene (2.5 mL) and water (2.5 mL), and a 35% by weight aqueous solution of methylhydrazine (0.197 mL, 2.3 mmol) was added thereto with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (93 mg, yield: 84%) composed of ethyl 1-methyl-3-trifluoro-methylpyrazole-4-carboxylate and ethyl 1-methyl-5-trifluoro-methylpyrazole-4-carboxylate. GC analysis revealed that the ratio of the former and the latter was 98:2.

Example 24

Ethyl 1-methyl-3-difluoromethylpyrazole-4-carboxylate was produced according to the following reaction formula:

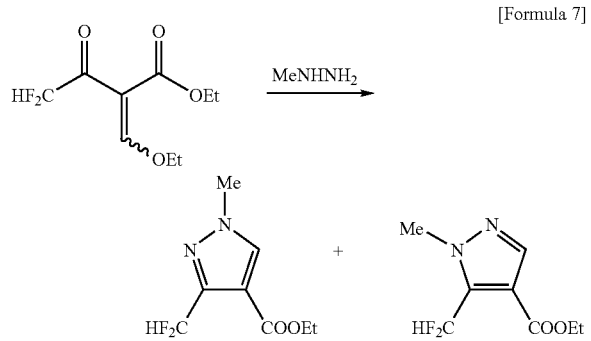

[Formula 7]

A 35% by weight aqueous solution of methylhydrazine (0.197 mL, 2.3 mmol) was added to a solution of sodium hydroxide (20 mg, 0.5 mmol) in water (5.0 mL) with stirring. To the solution, ethyl 2-ethoxymethylene-4,4-difluoroacetoacetate (0.091 mL, 111 mg, 0.5 mmol) was added dropwise under ice-cooling, followed by stirring for 1 hour at ambient temperature. To the reaction mixture, 1N hydrochloric acid was added to neutralize it, and a saturated aqueous solution of sodium chloride (20 mL) was further added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (88 mg, yield: 86%) composed of ethyl 1-methyl-3-difluoromethylpyrazole-4-carboxylate and ethyl 1-methyl-5-difluoromethylpyrazole-4-carboxylate. $^1$H-NMR spectra revealed that the ratio of the former and the latter was 94:6.

Ethyl 1-methyl-3-difluoromethylpyrazole-4-carboxylate; $^1$H-NMR (CDCl$_3$, TMS, ppm): δ1.35 (t, J=5.0 Hz, 3H), 3.97 (s, 1H), 4.32 (q, J=7.5 Hz, 2H), 7.10 (t, J$_{FH}$=54 Hz, 1H) 7.89 (s, 1H)

Ethyl 1-methyl-5-difluoromethylpyrazole-4-carboxylate; $^1$H-NMR (CDCl$_3$, TMS, ppm): δ1.35 (t, J=5.0 Hz, 3H), 3.97 (s, 1H), 4.32 (q, J=7.5 Hz, 2H), 7.49 (t, J$_{FH}$=54 Hz, 1H) 7.85 (s, 1H)

Example 25

Methylhydrazine (4.0 mL, 76.0 mmol) was added to a solution of potassium hydroxide (1.6 g, 28.5 mmol) in water (41 mL) with stirring. To the solution, ethyl 2-ethoxy-methylenedifluoroacetoacetate (6.5 g, 29.3 mmol) was added dropwise under ice-cooling, taking about 5 minutes, followed by stirring at the same temperature for 1 hour. After the reaction was completed, a solid deposited was taken by filtration, fully washed with water, and then, dried, thereby obtaining a white solid (5.17 g, yield: 87%). From $^1$H-NMR spectra and GC analysis, it was confirmed that this was an approximately pure product of ethyl 1-methyl-3-difluoromethyl-pyrazole-4-carboxylate. mp: 61 to 62° C., $^1$H-NMR (CDCl$_3$, TMS, ppm): δ1.33 (t, J=7.1 Hz, 1H), 3.97 (s, 3H), 4.32 (q, J=7.1 Hz, 2H), 7.10 (t, J$_{FH}$=54 Hz, 1H), 7.90 (s, 1H)

Example 26

Ethyl 1-ethyl-3-trifluoromethylpyrazole-4-carboxylate was produced according to the following reaction formula:

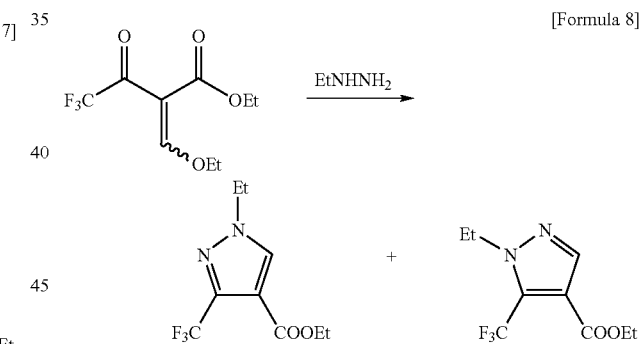

[Formula 8]

Water (5.0 mL) and a 35% by weight aqueous solution of ethylhydrazine (0.7 mL, 6.27 mmol) were added to an 18% aqueous solution of sodium hydroxide (0.8 mL, 4.4 mmol) with stirring. To the solution, a solution of ethyl 2-ethoxymethylene-trifluoroacetoacetate (1.0 g, 4.16 mmol) in toluene (5.0 mL) was added dropwise under ice-cooling, taking about 15 minutes, followed by stirring at the same temperature for 10 minutes. To the reaction mixture, 1N hydrochloric acid (20 mL) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (874 mg, yield: 89%) composed of ethyl 1-ethyl-3-trifluoromethylpyrazole-4-carboxylate and ethyl 1-ethyl-5-trifluoromethylpyrazole-4-carboxylate. GC analysis revealed that the ratio of the former and the latter was 89:11.

Ethyl 1-ethyl-3-trifluoromethylpyrazole-4-carboxylate; $^1$H-NMR (CDCl$_3$, TMS, ppm): δ1.35 (t, J=7.1 Hz, 3H), 1.54 (t, 7.4 Hz, 3H), 4.28 (q, J=7.8 Hz, 2H), 4.33 (q, J=7.1 Hz, 2H), 7.99 (s, 1H)

Ethyl 1-ethyl-5-trifluoromethylpyrazole-4-carboxylate; $^1$H-NMR (CDCl$_3$, TMS, ppm): δ1.35 (t, J=7.1 Hz, 3H), 1.54 (t, J=7.4 Hz, 3H), 4.28 (q, J=7.8 Hz, 2H), 4.33 (q, J=7.1 Hz, 2H), 7.93 (s, 1H)

Example 27

Ethyl 1-propyl-3-trifluoromethylpyrazole-4-carboxylate was produced according to the following reaction formula:

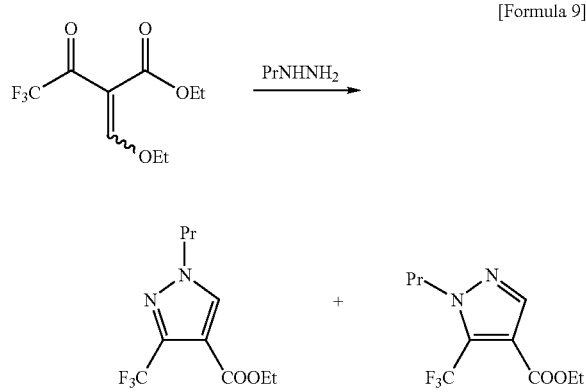

[Formula 9]

Water (5.0 mL) and a 35% by weight aqueous solution of propylhydrazine (0.9 mL, 6.54 mmol) were added to an 18% aqueous solution of sodium hydroxide (0.8 mL, 4.4 mmol) with stirring. To the solution, a solution of ethyl 2-ethoxymethylene-trifluoroacetoacetate (1.0 g, 4.16 mmol) in toluene (5.0 mL) was added dropwise under ice-cooling, taking about 5 minutes, followed by stirring at the same temperature for 10 minutes. To the reaction mixture, 1N hydrochloric acid (20 mL) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (1.02 g, yield: 98%) composed of ethyl 1-propyl-3-trifluoromethylpyrazole-4-carboxylate and ethyl 1-propyl-5-trifluoromethylpyrazole-4-carboxylate. GC analysis revealed that the ratio of the former and the latter was 86:14.

Ethyl 1-propyl-3-trifluoromethylpyrazole-4-carboxylate; $^1$H-NMR (CDCl$_3$, TMS, ppm): δ0.94 (t, J=5.0 Hz, 3H), 1.35 (t, 7.1 Hz, 3H), 1.93 (q, J=7.3 Hz, 2H), 4.13 (t, J=7.1 Hz, 2H), 4.32 (q, J=7.1 Hz, 2H), 8.0 (s, 1H)

Ethyl 1-propyl-5-trifluoromethylpyrazole-4-carboxylate; $^1$H-NMR (CDCl$_3$, TMS, ppm): δ0.94 (t, J=5.0 Hz, 3H), 1.35 (t, J=7.1 Hz, 3H), 1.93 (q, J=7.3 Hz, 2H), 4.13 (t, J=7.1 Hz, 2H), 4.32 (q, J=7.1 Hz, 2H), 7.92 (s, 1H)

Example 28

Ethyl 1-isobutyl-3-trifluoromethylpyrazole-4-carboxylate was produced according to the following reaction formula:

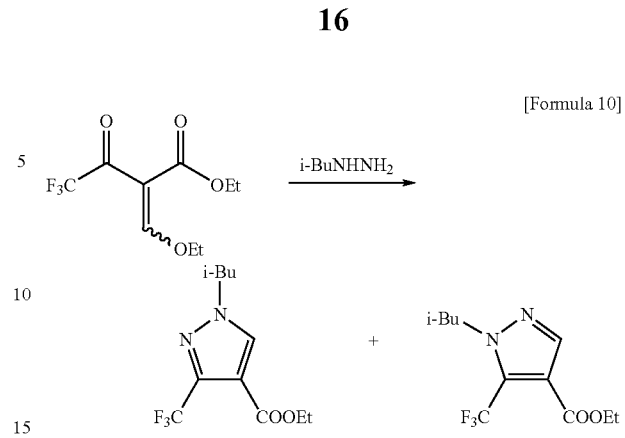

[Formula 10]

Water (5.0 mL) and a 35% by weight aqueous solution of isobutylhydrazine (1.0 mL, 6.12 mmol) were added to an 18% aqueous solution of sodium hydroxide (0.8 mL, 4.4 mmol) with stirring. To the solution, a solution of ethyl 2-ethoxy-methylenetrifluoroacetoacetate (1.0 g, 4.16 mmol) in toluene (5.0 mL) was added dropwise under ice-cooling, followed by stirring at the same temperature for 10 minutes. To the reaction mixture, 1N hydrochloric acid (20 mL) was added, followed by extraction with ethyl acetate (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture (1.06 g, yield: 96%) composed of ethyl 1-isobutyl-3-trifluoromethylpyrazole-4-carboxylate and ethyl 1-isobutyl-5-trifluoromethylpyrazole-4-carboxylate. GC analysis revealed that the ratio of the former and the latter was 77:23.

Ethyl 1-isobutyl-3-trifluoromethylpyrazole-4-carboxylate; $^1$H-NMR (CDCl$_3$, TMS, ppm): δ0.93 (t, J=3.8 Hz, 3H), 1.33 (t, J=7.1 Hz, 3H), 3.95 (d, J=7.3 Hz, 2H), 4.15 (d, J=7.1 Hz, 2H), 4.32 (q, J=7.0 Hz, H), 7.94 (s, 1H)

Ethyl 1-isobutyl-5-trifluoromethylpyrazole-4-carboxylate; $^1$H-NMR (CDCl$_3$, TMS, ppm): δ0.93 (t, J=3.8 Hz, 3H), 1.33 (t, J=7.1 Hz, 3H), 4.14 (d, J=7.3 Hz, 2H), 4.15 (d, J=7.1 Hz, 2H), 4.32 (q, J=7.0 Hz, H), 7.94 (s, 1H)

Comparative Example 1

A 35% by weight aqueous solution of methylhydrazine (0.197 mL, 2.3 mmol) was added to water (5.0 mL) with stirring. To the solution, ethyl 2-ethoxymethylene-4,4,4-trifluoro-acetoacetate (0.097 mL, 120 mg, 0.5 mmol) was added dropwise under ice-cooling, followed by stirring for 1 hour at ambient temperature. To the reaction mixture, a saturated aqueous solution of sodium chloride (20 mL) was added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (101 mg, yield: 91%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 66:34.

Comparative Example 2

Ethyl 2-ethoxymethylenetrifluoroacetoacetate (1.0 g, 4.16 mmol) was added dropwise to a solution of methylhydrazine (0.19 mL, 3.61 mmol) in water (10 mL) at 50° C., taking 5 minutes, followed by stirring at the same temperature for 10 minutes. The reaction mixture was extracted with ether (30 mL×3), and the organic layer was dried over anhydrous magnesium sulfate. The desiccant was separated by filtration, and then, the solvent was removed from the filtrate by distillation under reduced pressure, thereby obtaining a mixture composed of ethyl 1-methyl-3-trifluoromethylpyrazole-4-carboxylate and ethyl 1-methyl-5-trifluoromethylpyrazole-4-carboxylate approximately quantitatively. GC analysis revealed that the ratio of the former and the latter was 63:37.

Comparative Example 3

Methylhydrazine (69 mg, 1.5 mmol) was added to ethanol (5.0 mL) with stirring. To the solution, ethyl 2-ethoxymethylene-4,4,4-trifluoroacetoacetate (0.097 mL, 120 mg, 0.5 mmol) was added dropwise under ice-cooling, followed by stirring for 1 hour at ambient temperature. To the reaction mixture, a saturated aqueous solution of sodium chloride (20 mL) was added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (103 mg, yield: 93%) composed of ethyl 1-methyl-3-trifluoromethylpyrazole-4-carboxylate and ethyl 1-methyl-5-trifluoromethylpyrazole-4-carboxylate. GC analysis revealed that the ratio of the former and the latter was 76:24.

Comparative Example 4

Methylhydrazine (69 mg, 1.5 mmol) was added to ethyl acetate (5.0 mL) with stirring. To the solution, ethyl 2-ethoxymethylene-4,4,4-trifluoroacetoacetate (0.097 mL, 120 mg, 0.5 mmol) was added dropwise at room temperature, followed by stirring for 1 hour at ambient temperature. To the reaction mixture, a saturated aqueous solution of sodium chloride (20 mL) was added, followed by extraction with chloroform (20 mL×3). The organic layer was dried over anhydrous sodium sulfate, and the desiccant was separated by filtration. Then, the filtrate was evaporated to dryness under reduced pressure, thereby obtaining a white solid (91 mg, yield: 82%) composed of ethyl 1-methyl-3-trifluoromethylpyrazole-4-carboxylate and ethyl 1-methyl-5-trifluoromethylpyrazole-4-carboxylate. $^1$H-NMR spectra revealed that the ratio of the former and the latter was 85:15.

Comparative Example 5

Methylhydrazine (69 mg, 1.5 mmol) was added to a mixed solution of ethyl acetate (5.0 mL) and water (5.0 mL) with stirring. To the solution, ethyl 2-ethoxymethylene-4,4,4-trifluoroacetoacetate (0.097 mL, 120 mg, 0.5 mmol) was added dropwise at room temperature, followed by stirring for 1 hour. To the reaction mixture, a saturated aqueous solution of sodium chloride (20 mL) was added, followed by extraction with ethyl acetate (20 mL×3). The organic layer was dried over anhydrous sodium sulfate, and the desiccant was separated by filtration. Then, the filtrate was evaporated to dryness under reduced pressure, thereby obtaining a white solid (103 mg, yield: 93%) composed of ethyl 1-methyl-3-trifluoro-methylpyrazole-4-carboxylate and ethyl 1-methyl-5-trifluoromethylpyrazole-4-carboxylate. GC analysis revealed that the ratio of the former and the latter was 79:21.

Comparative Example 6

A solution of ethyl 2-ethoxymethylenetrifluoroaceto-acetate (1.0 g, 4.16 mmol) in toluene (5.0 mL) was added dropwise to a solution of methylhydrazine (0.19 mL, 3.61 mmol) in water (5.0 mL) under ice-cooling, taking 10 minutes, followed by stirring at the same temperature for 10 minutes. To the reaction mixture, 1N hydrochloric acid (10 mL) was added, followed by extraction with toluene (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture composed of ethyl 1-methyl-3-trifluoromethylpyrazole-4-carboxylate and ethyl 1-methyl-5-trifluoromethylpyrazole-4-carboxylate approximately quantitatively. GC analysis revealed that the ratio of the former and the latter was 81:19.

Comparative Example 7

A solution of ethyl 2-ethoxymethylenetrifluoroaceto-acetate (1.0 g, 4.16 mmol) in toluene (5.0 mL) was added dropwise to a solution of methylhydrazine (0.19 mL, 3.61 mmol) in water (5.0 mL) at 50° C., followed by stirring at the same temperature for 10 minutes. To the reaction mixture, 1N hydrochloric acid (10 mL) was added, followed by extraction with toluene (30 mL×3). The organic layer was washed with a saturated aqueous solution of sodium chloride (30 mL), and dried over anhydrous magnesium sulfate. After the desiccant was separated by filtration, the solvent was removed from the filtrate by distillation under reduced pressure, thereby obtaining a mixture composed of ethyl 1-methyl-3-trifluoromethylpyrazole-4-carboxylate and ethyl 1-methyl-5-trifluoromethylpyrazole-4-carboxylate approximately quantitatively. GC analysis revealed that the ratio of the former and the latter was 74:26.

Comparative Example 8

A solution of ethyl 2-ethoxymethylenetrifluoroaceto-acetate (1.0 g, 4.16 mmol) in toluene (5.0 mL) was added dropwise to a solution of propylhydrazine (378 mg, 4.99 mmol) in water (5.0 mL) under ice-cooling, taking about 5 minutes, followed by stirring at the same temperature for 10 minutes. To the reaction mixture, 1N hydrochloric acid (10 mL) was added, followed by extraction with toluene (20 mL×3). The organic layer was dried over anhydrous magnesium sulfate, and the desiccant was separated by filtration. Then, the solvent was removed from the filtrate by distillation under reduced pressure, thereby obtaining a mixture composed of ethyl 1-propyl-3-trifluoromethylpyrazole-4-carboxylate and ethyl 1-propyl-5-trifluoromethylpyrazole-4-carboxylate approximately quantitatively. GC analysis revealed that the ratio of the former and the latter was 76:24.

Comparative Example 9

A solution of ethyl 2-ethoxymethylenetrifluoroaceto-acetate (1.2 g, 5.0 mmol) in toluene (5.0 mL) was added dropwise to a solution of isobutylhydrazine (550 mg, 6.24 mmol) in water (5.0 mL) under ice-cooling, taking 5 minutes, followed by stirring at the same temperature for 10 minutes. To the reaction mixture, 2N hydrochloric acid (5 mL) was added, followed by extraction with toluene (20 mL×3). The organic layer was dried over anhydrous magnesium sulfate, and the desiccant was separated by filtration. Then, the solvent was removed from the filtrate by distillation under reduced pressure, thereby obtaining a mixture (1.28 g, yield: 78%) composed of ethyl 1-isobutyl-3-trifluoromethylpyrazole-4-carboxylate and ethyl 1-isobutyl-5-trifluoromethylpyrazole-4-carboxylate. GC analysis revealed that the ratio of the former and the latter was 62:38.

The invention claimed is:

1. A process for producing 1-substituted-3-fluoro-alkylpyrazole-4-carboxylate in which 2-alkoxy-methylenefluoroacylacetate represented by general formula (1):

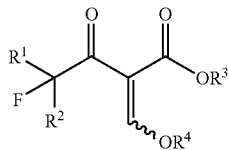
(1)

wherein $R^1$ represents a hydrogen atom or a halogen atom, $R^2$ represents a hydrogen atom, a fluorine atom or an alkyl group having 1 to 12 carbon atoms, which may be substituted with a chlorine atom or a fluorine atom, and $R^3$ and $R^4$ each independently represents an alkyl group having 1 to 6 carbon atoms, and a hydrazine represented by general formula (2):

$R^5NHNH_2$   (2)

wherein $R^5$ represents an alkyl group having 1 to 6 carbon atoms, which may be substituted, are reacted with each other in a water solvent or a mixed solvent of water and an organic solvent to produce 1-substituted-3-fluoroalkylpyrazole-4-carboxylate represented by general formula (3):

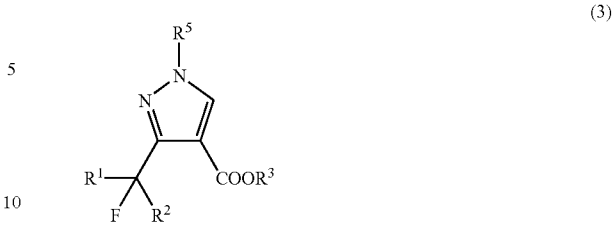

wherein $R^1$, $R^2$, $R^3$ and $R^5$ have the same meanings as described above, wherein the process is characterized by the reaction being conducted in the presence of a base, wherein the base is selected from alkali metal hydroxides and alkali earth metal hydroxides.

2. The process for producing 1-substituted-3-fluoroalkylpyrazole-4-carboxylate according to claim 1, wherein the base is sodium hydroxide or potassium hydroxide.

3. The process for producing 1-substituted-3-fluoro-alkylpyrazole-4-carboxylate according to claim 1, wherein the amount of the base used is from 0.001 to 10.0 equivalents based on 2-alkoxymethylenefluoroacylacetate as a reaction substrate, which is represented by general formula (1).

4. The process for producing 1-substituted-3-fluoroalkylpyrazole-4-carboxylate according to claim 1, wherein the weight ratio of 2-alkoxy-methylenefluoroacylacetate represented by general formula (1) and water is from 1/0.25 to 1/100.

5. The process for producing 1-substituted-3-fluoroalkylpyrazole-4-carboxylate according to claim 1, wherein the organic solvent is at least one member selected from the group consisting of aromatic hydrocarbons, aliphatic hydrocarbons, alcohols, esters and halogenated hydrocarbons.

6. The process for producing 1-substituted-3-fluoro-alkylpyrazole-4-carboxylate according to claim 1, wherein the reaction temperature is from −30 to 80° C.

* * * * *